United States Patent [19]
Lower et al.

[11] Patent Number: 5,613,971
[45] Date of Patent: Mar. 25, 1997

[54] RATCHETING TIBIAL AND FEMORAL GUIDE

[75] Inventors: Jerry L. Lower, Bourbon, Ind.; John Balestrieri, Greenfield, Wis.

[73] Assignee: Depuy Inc., Warsaw, Ind.

[21] Appl. No.: 513,728

[22] Filed: Aug. 11, 1995

[51] Int. Cl.$^6$ .................................................. A61B 17/58
[52] U.S. Cl. .............................. 606/96; 606/98; 606/102; 606/89
[58] Field of Search .................. 606/86, 87, 88, 606/96, 97, 98, 102, 103

[56] References Cited

U.S. PATENT DOCUMENTS

| | | | |
|---|---|---|---|
| 4,034,746 | 7/1977 | Williams | 128/17 |
| 4,254,763 | 3/1981 | McCready et al. | 128/20 |
| 4,344,420 | 8/1982 | Forder | 128/20 |
| 5,000,163 | 3/1991 | Ray et al. | 128/20 |
| 5,163,940 | 11/1992 | Bourque | 606/88 |
| 5,312,412 | 5/1994 | Whipple | 606/96 |
| 5,350,380 | 9/1994 | Goble et al. | 606/80 |
| 5,354,300 | 10/1994 | Goble et al. | 606/80 |

OTHER PUBLICATIONS

"PRO-*TRAC*", Acufex Micosurgical, Inc. Advertisement, one page, date prior to Aug. 11, 1995.
"Restore™ ACL Instrument System", DePuy Inc. brochure, 1992.

*Primary Examiner*—Michael Powell Buiz
*Assistant Examiner*—Mark S. Leonardo
*Attorney, Agent, or Firm*—Barnes & Thornburg

[57] ABSTRACT

A bone drill guide having at least a first arm slidable within a bore of the body of the drill guide and a ratchet mechanism for locking the first arm and the first bore. The ratchet mechanism includes teeth on the first arm and a pawl biased along a first axis and having a continuous engagement edge for engaging the teeth of the first arm for any angular orientation of the pawl about the first axis. The continuous engagement edge is a curve in a plane transverse to the first axis for providing a substantially renewable point contact with the teeth. The recess includes side walls tapered towards the engagement edge to allow a narrow contact at the engagement edge and re-enforce face walls to absorb the axial forces of the guide.

20 Claims, 2 Drawing Sheets

U.S. Patent  Mar. 25, 1997  Sheet 1 of 2  5,613,971
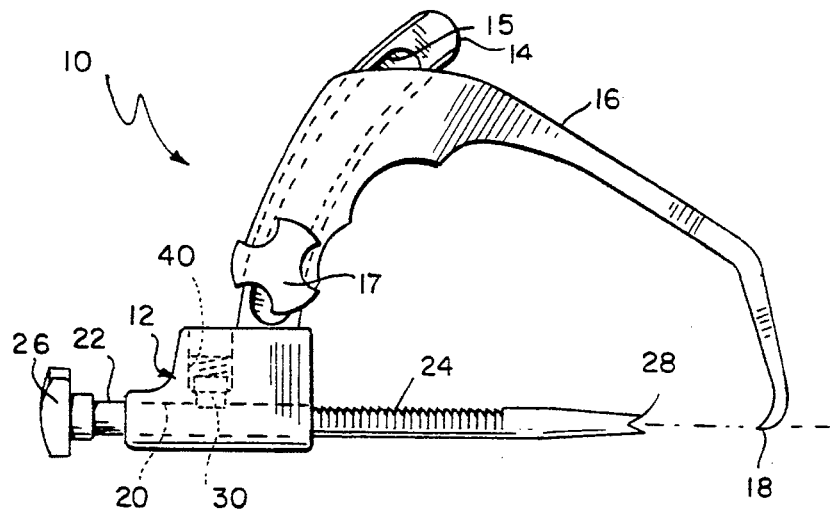
FIG. 1
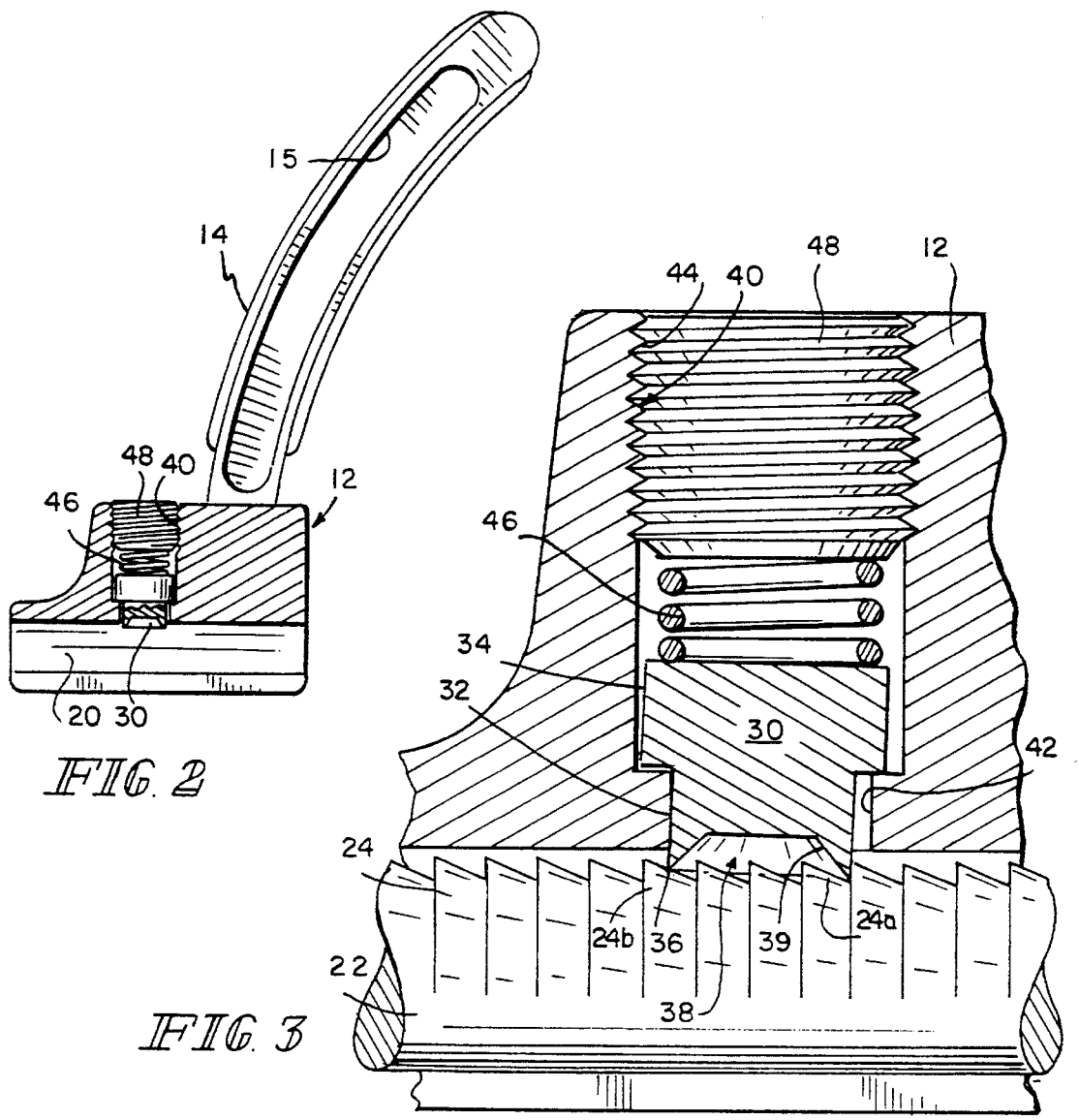
FIG. 2
FIG. 3

RATCHETING TIBIAL AND FEMORAL GUIDE

BACKGROUND AND SUMMARY OF THE INVENTION

The present invention relates generally to drill guide apparatus for bone drilling tools and more specifically to an improved ratchet mechanism for bone drilling tools.

When a ligament, such as an anterior cruciate ligament (ACL) of a knee is damaged or torn, a replacement ligament is often installed in the knee to reconstruct the natural anterior cruciate ligament. During such reconstruction, a tunnel is drilled through the anterior portion of the tibia upwardly through the tibia plateau and into the distal end of the femur to approximate the natural position of the anterior cruciate ligament. A bone-ligament-bone graft is then harvested from the patellar tendon following standard procedures. Typically, a rectangular in length and trapezoid in cross-section shaped graph is cut and contoured using a graft sizer. Sutural holes are then drilled in the graft. The graft is then installed in the drilled tunnel.

The prior art includes different types of drill guides for locating tunnels in the femur and tibia for aligning and installing transverse pins to anchor the ligament replacement. One such drill guide is illustrated in U.S. Pat. No. 5,354,300. The locking mechanism for the drill guide shown therein includes a spring cog having a knife edge on the interior of a bore engaging the teeth on the drill guide movable within the bore. Although this particular mechanism works very well, it is expensive to make the knife edge in the interior of the bore. Also, since the knife edge is linear, angular orientation of this edge is important to the efficient operation of the locking mechanism. Although the knife edge may provide a substantially point contact to the teeth of the drill guide, this point contact will wear and is not adjustable to provide a fresh point contact edge.

Other types of tibial end femoral drill guides are available, for example, Restore ACL Instrument System from DePuy of Warsaw, Ind. This requires two hands to operate, one to push the drill guide and the other to operate the latch which is a cam operated or friction lock structure.

Thus, it is an object of the present invention to provide a adjustable drill guide operable with one hand and at a reduced expense.

Another object of the present invention is to provide a drill guide operable with one hand and a less complicated locking mechanism.

A still further object of the present invention is to provide a locking mechanism for an adjustable drill guide having a renewable contact surface.

These and other objects are achieved by providing at least a first arm slidable within a bore of the body of the drill guide and a ratchet mechanism for locking the first arm and the first bore. The ratchet mechanism includes teeth on the first arm and a pawl biased along a first axis and having a continuous engagement edge for engaging the teeth of the first arm for any angular orientation of the pawl about the first axis. The continuous engagement edge is a curve in a plane transverse to the first axis for providing a substantially renewable point contact with the teeth. The recess includes side walls tapered towards the engagement edge to allow a narrow contact at the engagement edge and re-enforce face walls to absorb the axial forces of the guide.

The pawl is a cylinder with a recess in a first end of a first diameter forming the engagement edge. The pawl includes a head at the second end of a second diameter greater than the first diameter. The body includes a second bore having a first and second portions of third and fourth diameters greater than the first and second diameters and joined by a shoulder. The difference between the third and fourth and the first and second diameters is sufficient to allow the pawl to cant transverse to the biasing axis of the pawl.

The first arm rotates in the first bore and includes teeth only of a portion of its transverse periphery. This allows the first arm to be retracted by rotating into the non-tooth side. The first arm is preferably hollow for receiving the drill. A second arm with the same locking arrangement may also be provided. Depending upon the specific instrument used, the first and second arms are either transverse to each other or are co-linear.

Other objects, advantages and novel features of the present invention will become apparent from the following detailed description of the invention when considered in conjunction with the accompanying drawings.

BRIEF DESCRIPTION OF THE DRAWINGS

FIG. 1 is a side view of a tibial drill guide incorporating the lock of the present invention.

FIG. 2 is a cross-section of the tibial drill guide of FIG. 1.

FIG. 3 is an enlarged view of the locking mechanism of the present invention.

BRIEF DESCRIPTION OF THE PREFERRED EMBODIMENTS

Figure 4:
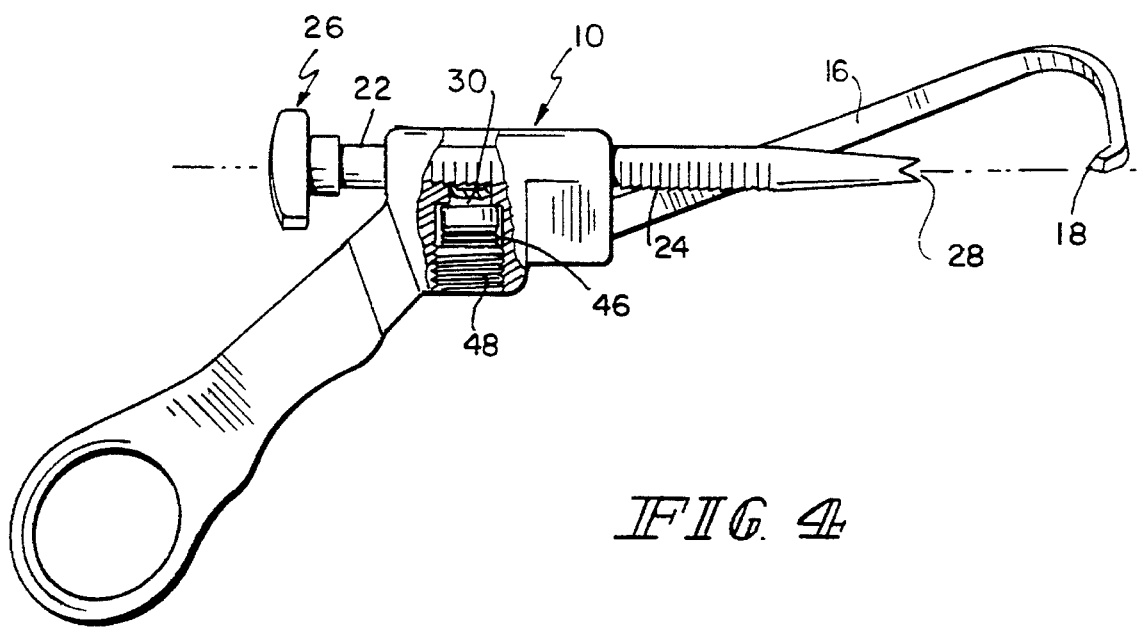
FIG. 4 is a side view of a femoral drill guide incorporating the latch of the present invention.

A tibial drill guide 10 as illustrated in FIG. 1 is including a body 12 having a guide slide 14 extending therefrom and an arm 16 slidable on the guide 14 and terminating at a tip 18. Slide 14 includes an arcuate opening 15 to receive a cam lock 17 carried by the arm 16. Body 12 includes a bore 20 receiving a hollow drill guide 22 therein. The drill guide 22 includes teeth 24 on a portion of its circumference, preferably no more than 180 degrees. A knob 26 on one end of the drill guide 22 allows rotation of the drill guide 22 within the bore 20. The other end of the drill guide is serrated at 28. The axis of the bore 20 and the drill guide 22 are co-linear with the axis of tip 18 of arm 16.

A ratchet or lock mechanism includes a pawl 30 cooperating with the teeth 24 on the drill guide 22 to lock it in various extended positions with respect to the body 12. The pawl 30 lies within a bore 40 in the body 12. As illustrated more specifically in FIG. 2, a spring 46 also in the bore 40, biases the pawl 30 into the drill guide 22. A removable spring stop 48 is threadably received in the bore 40.

As illustrated in FIG. 3, the pawl 30 includes a first cylindrical section 32 of the first diameter and a second cylindrical section or head 34 of a second diameter larger than the first diameter. The first section 32 terminates in an engagement edge 36 formed by a recess 38. The side walls 39 of the recess 38 are tapered so as to provide a narrow engagement edge 36 while allowing the thickness of the remainder of the wall to be sufficient to withstand the axial forces of the drill guide 22 in the bore 20.

The bore 40 includes a first section 42 of a first diameter and a second section 44 of a second diameter larger than the first diameter. The difference between the diameters of 32 and 42 and of 34 and 44 are sufficient to allow the pawl 30 to cant relative to the axis of the bore 40. As is evident from FIG. 3, when the front of the engagement edge 36 engages one of the teeth 24a on the guide 22, the opposed portion of edge 26 will engage a second tooth 24b at a different elevation. This will produce a canting of the pawl 30.

Preferably, the spacing of the teeth 24 matches the diameter of the continuous circular edge 36. By way of example, the pawl sections 32 and 34 may have a diameter of 0.22 and 0.30 inches respectively and the bore sections 42 and 44 may have a diameter of 0.25 and 0.332 respectively. The bore may be a depth of 0.04 inches and side walls tapered at 45 degrees. The spacing of teeth 24 may be 0.040 inches and a height of 0.030 inches. The recess 38 is made very simply by a drilling operation which requires no special machines or tooling.

In operation, the drill guide 22 may be forced forward by the thumb of the hand holding the body 12 and secure the tibial bone between point 18 of arm 16 and the end 28 of the guide 22. The tool guide 22 is locked in place by the engagement of the pawl 30 in the teeth 24. To remove the drill guide 10 from the tibial, the handle 26 is rotated such that the non-toothed surface of the drill guide 22 is adjacent to the pawl 30. The guide 22 may then be slid backward through the bore 20.

By using a continuous engagement edge 36, the angular orientation of the pawl 30 with respect to the bore 40 does not effect the operation of a pawl with the teeth 24. It should also be noted that any rotation of the pawl 30 within the bore 40 allows a fresh engagement edge to be available for intersection with the valley between the teeth 24. A contact between the engagement edge 36 and the valley of the teeth is considered a point contact.

FIG. 4 shows the pawl illustrated in FIG. 3 incorporated in a femoral drill guide. Those portions having similar functions have the same numbers as used in FIG. 3 and will not be described in detail.

Figure 5:
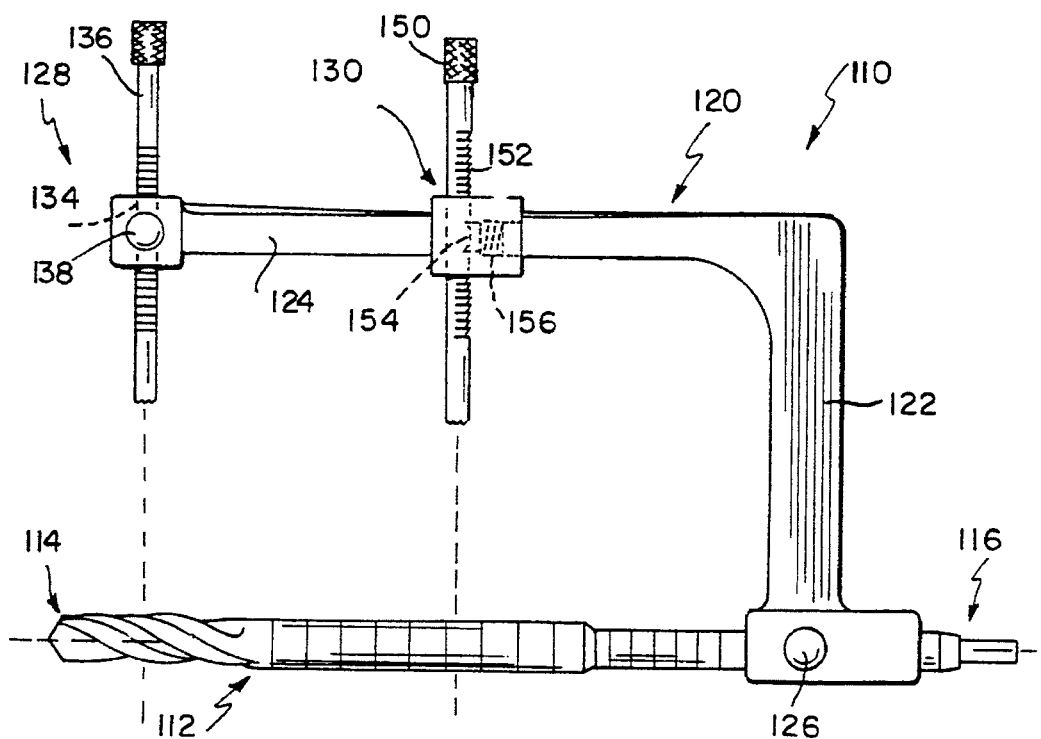
FIG. 5 is a elevation view of a drill guide apparatus of U.S. Pat. No. 5,350,380 incorporating the lock of the present invention.

FIG. 5 illustrates the drill guide of U.S. Pat. No. 5,350,380. The drill guide apparatus 110 includes a tunnel drill 112 within first end 114 for cutting the bone and a second end 116 for attachment of a driver. The drill 112 is received within a bore in a first arm 122 of a body 120, also having a second arm 124. A locking mechanism 126 permanently sliding movement of the body 120 on the drill 112. Locking mechanism 126 is that of the prior art and not of the present invention.

The drill guide apparatus 110 includes a femur drill guide 128 and a tibia drill guide 130 received in bores in the arm 124. A drill sleeve 136 is adjustably positioned in a bore 134 and includes a latch mechanism 138 of that illustrated in FIG. 3. The tibia drill sleeve 150 has teeth 152 on its surface to interact with pawl 154 which is biased by spring 156. The latch mechanism including the pawl 154 into spring 156 is that illustrated in FIG. 3.

As discussed for FIGS. 1–4, the tibia and femur guides of FIG. 5 may be operated by a single hand pushing the drill guides towards the bone with the thumb or other finger which is already holding the tool 110. To release the guides, they are rotated approximately 180 degrees. The continuous engagement of the pawls provide a continuously renewable surface and its operation is independent of the angular position of the pawl.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A guide for a bone drilling tool comprising:

a body having first and second arms positioned to secure the tool to a bone;

said first arm slides within a first bore in said body;

a ratchet for locking said first arm in said first bore, said ratchet including teeth on said first arm and a pawl in said body biased along a first axis to engage said teeth; and said pawl being rotatable about said first axis and including a continuous engagement edge for lockingly engaging said teeth for all angular orientations of said pawl about said first axis.

2. A guide according to claim 1, wherein said pawl is cylindrical with a recess in a first end of a first diameter forming said engagement edge.

3. A guide according to claim 2, wherein:

said pawl includes a head at its second end of a second diameter greater than the first diameter of the first end; and said body includes a second bore having first and second portions of third and fourth diameters and joined by a shoulder.

4. A guide according to claim 3, wherein said third and fourth diameters are sufficiently greater than said first and second diameters respectively to allow said pawl to cant transverse to said first axis.

5. A guide according to claim 2, wherein said recess includes side walls tapered towards said engagement edge.

6. A guide according to claim 1, wherein said first arm rotates in said first bore and includes teeth on only a portion of its transverse periphery.

7. A guide according to claim 1, wherein said first arm is hollow for receiving a drill.

8. A guide according to claim 1, wherein said second arm slides within a second bore in said body and includes teeth; and including a second pawl in said body biased along a second axis and having a continuous engagement edge for engaging said teeth for any angular orientation of said pawl about said second axis.

9. A guide according to claim 1, wherein said first and second arms are transverse to each other.

10. A guide according to claim 1, wherein said first and second arms are collinear.

11. A guide according to claim 1, wherein said engagement edge is curved in a plane transverse to said first axis for engaging said teeth at a renewable point.

12. A guide for a bone drilling tool comprising:

a body having first and second arms positioned to secure the tool to a bone;

said first arm slides within a first bore in said body;

a ratchet for locking said first arm in said first bore, said ratchet including teeth on said first arm and a pawl in said body biased along a first axis; and said pawl being rotatable about said first axis and including an engagement edge curved in a plane transverse to said first axis for lockingly engaging said teeth at a renewable point.

13. A guide according to claim 12, wherein said pawl is cylindrical with a recess in a first end of a first diameter forming said engagement edge.

14. A guide according to claim 13, wherein:
said pawl includes a head at its second end of a second diameter greater than the first diameter of the first end; and
said body includes a second bore having first and second portions of third and fourth diameters and joined by a shoulder.

15. A guide according to claim 14, wherein said third and fourth diameters are sufficiently greater than said first and second diameters respectively to allow said pawl to cant transverse to said first axis.

16. A guide according to claim 13, wherein said recess includes side walls tapered towards said engagement edge.

17. A guide according to claim 12, wherein said first arm rotates in said first bore and includes teeth on only a portion of its transverse periphery.

18. A guide according to claim 12, wherein said first arm is hollow for receiving a drill.

19. A guide according to claim 12, wherein said second arm slides within a second bore in said body and includes teeth; and
including a second pawl in said body biased along a second axis and having an engagement edge curved in a plane transverse to said second axis for engaging said teeth at a renewable point.

20. A guide according to claim 12, wherein said engagement edge is curved in a plane transverse to said first axis for engaging said teeth at a renewable point.

* * * * *